United States Patent [19]

Seubert

[11] 4,362,875

[45] Dec. 7, 1982

[54] PROCESS FOR PREPARING (1-ACYLAMINOMETHYL)-1,2,3,4-TETRAHYDROISOQUINOLINES

[75] Inventor: Jürgen Seubert, Darmstadt, Fed. Rep. of Germany

[73] Assignee: Merck Patent Gesellschaft mit beschrankter Haftung, Darmstadt, Fed. Rep. of Germany

[21] Appl. No.: 967,046

[22] Filed: Dec. 6, 1978

Related U.S. Application Data

[60] Division of Ser. No. 877,436, Feb. 13, 1978, abandoned, which is a continuation of Ser. No. 651,856, Jan. 23, 1976, abandoned.

[30] Foreign Application Priority Data

Feb. 1, 1975 [DE] Fed. Rep. of Germany ....... 2504250

[51] Int. Cl.$^3$ .................... C07D 217/16; A61K 31/47
[52] U.S. Cl. .................................... 546/146; 424/250; 424/258; 544/344; 546/144
[58] Field of Search ................................ 546/144, 146

[56] References Cited

U.S. PATENT DOCUMENTS 3,985,881 10/1976 Mehrhof et al. ................... 546/146
4,118,494 10/1978 Kunstmann et al. ............... 546/141

Primary Examiner—Donald G. Daus
Assistant Examiner—James H. Turnipseed
Attorney, Agent, or Firm—Millen & White

[57] ABSTRACT

Novel tetrahydroquinolines of the formula

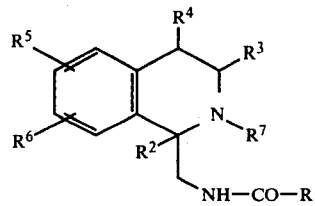

wherein R is cycloalkyl or cycloalkenyl each containing 4–7 ring carbon atoms and the cycloalkyl optionally being substituted by one of methyl, hydroxyl or oxo; phenyl substituted by 1–2 of amino, acylamino of up to 4 carbon atoms, Hal, hydroxyl, methoxy or nitro, wherein Hal is fluorine, chlorine, bromine or iodine; thienyl; pyridyl; tetrahydropyranyl; tetrahydrothiopyranyl; and when at least one of $R^2$, $R^3$, $R^4$, $R^5$ or $R^6$ is other than H, also phenyl; $R^2$, $R^3$ and $R^4$ each are H or methyl; $R^5$ and $R^6$ each are H, methyl or methoxy; $R^7$ is H or —CO—CH$_2$—X wherein X is chlorine, bromine or iodine; the acid addition salts thereof; which compounds are useful as antihelmintics and as intermediates for the production of 2-acyl-4-oxo-1,2,3,6,7,11b-hexahydro-4H-pyrazino-[2,1-a]isoquinoline derivatives; and the corresponding compounds wherein R is alkyl of 1–6 carbon atoms, phenyl substituted by three of the substituents named above, and phenyl when all of $R^2$, $R^3$, $R^4$, $R^5$ and $R^6$ are H; are produced by acylating the corresponding 1-aminomethyl-1,2,3,4-tetrahydroisoquinoline wherein $R^7$ is H, and optionally thereafter reducing the R group and/or reacting the ring nitrogen atom with an acylating group.

6 Claims, No Drawings

PROCESS FOR PREPARING (1-ACYLAMINOMETHYL)-1,2,3,4-TETRAHYDROISOQUINOLINES

This is a division or application Ser. No. 877,436, filed Feb. 13, 1978 now abandoned which in turn is a continuation of Ser. No. 651,856, filed on Jan. 23, 1976 now abandoned.

BACKGROUND OF THE INVENTION

This invention relates to novel tetrahydroisoquinoline derivatives, to processes for their production and use, and to intermediates useful in the production thereof.

In U.S. patent applications Ser. No. 533,467, filed Dec. 16, 1974 now U.S. Pat. No. 4,001,411 and Ser. No. 607,810, filed Aug. 26, 1975, now U.S. Pat. No. 4,051,243 and in German Patent Applications P 23 62 539.0 and P 24 41 261.1, there are described processes for the preparation of 2-acyl-4-oxo-1,2,3,6,7,11b-hexahydro-4H-pyrazino[2,1-a]isoquinolines starting from 1-acylaminomethyl-2-halo-acetyl-1,2,3,4-tetrahydroisoquinolines. The last-mentioned compounds are obtainable from the known 1-cyano-2-acyl-1,2-dihydro- or -1,2,3,4-tetrahydro-isoquinolines by hydrogenation in the presence of Raney nickel and subsequent reaction with a haloacetyl halide.

Some of the compounds of Formula I hereinafter which are excluded from Formula Ia are known from the U.S. Patent Applications mentioned above.

It has been found that even the starting materials for this reaction sequence, viz., the 1-cyano-2-acyl-1,2-dihydro- or -1,2,3,4-tetrahydroisoquinolines are frequently obtainable in yields which are technically not satisfactory. For example, 1-cyano-2-cyclohexylcarbonyl-1,2-dihydroisoquinoline is formed only in small amounts from isoquinoline, cyclohexanecarboxylic acid chloride and cyanides.

The hydrogenation of the 1-cyano-2-acyl-1,2-dihydro- or -1,2,3,4-tetrahydroisoquinolines in the presence of Raney nickel also does not proceed satisfactorily. Thus, from the reaction mixture which results in the case of the hydrogenation of 1-cyano-2-benzoyl-1,2-dihydroisoquinoline, a maximum of only 50% of 1-benzamidomethyl-TIS can be isolated.

It is an object of this invention to provide a novel, advantageous process for the preparation of 1-acylaminomethyl-1,2,3,4-tetrahydroisoquinolines as defined hereinafter.

A further object of this invention is to provide novel tetrahydroisoquinolines useful as pharmaceuticals in human and veterinary medicine.

Other objects will be apparent to those skilled in the art.

A further object of this invention is the provision of a novel synthesis for the preparation of 2-acyl-4-oxo-1,2,3,6,7,11b-hexahydro-4H-pyrazino-[2,1-a]isoquinoline derivatives which are outstandingly effective antihelmintically.

For the sake of brevity, hereinafter the designation "-TIS" is employed to mean "-1,2,3,4-tetrahydroisoquinoline." Consequently, e.g., the compound "1-cyclohexylcarboxamidomethyl-1,2,3,4-tetrahydroisoquinoline" can be designated as "1-cyclohexylcarboxamidomethyl-TIS."

SUMMARY OF THE INVENTION

In a process aspect, this invention relates to a process for the production of tetrahydroisoquinoline derivatives of the general Formula I

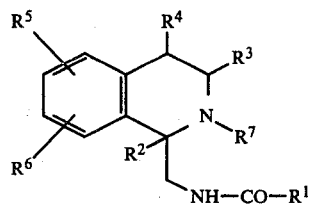

wherein $R^1$ is alkyl of 1–6 carbon atoms; cycloalkyl or cycloalkenyl each containing 4–7 ring carbon atoms and the cycloalkyl optionally being substituted by one of methyl, hydroxyl and oxo; phenyl; phenyl substituted by 1–3 of amino, acylamino of up to 4 carbon atoms, Hal, hydroxyl, methoxy and nitro, wherein Hal is fluorine, chlorine, bromine or iodine; thienyl; pyridyl; tetrahydropyranyl; or tetrahydrothiopyranyl; $R^2$, $R^3$ and $R^4$ each are H or methyl; $R^5$ and $R^6$ each are H, methyl or methoxy; $R^7$ is H or $-CO-CH_2-X$, wherein X is chlorine, bromine or iodine; and the acid addition salts thereof.

In a composition aspect, this invention relates to novel tetrahydroisoquinoline derivatives of the general Formula Ia

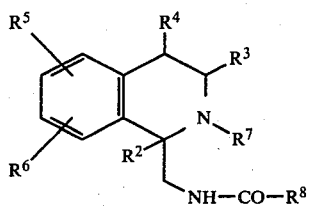

wherein $R^2$ through $R^7$ and Hal have the values given for Formula I and $R^8$ is cycloalkyl or cycloalkenyl; each containing 4–7 ring carbon atoms and the cycloalkyl optionally being substituted by one of methyl, hydroxyl or oxo; phenyl substituted by 1–2 of amino, acylamino of up to 4 carbon atoms, Hal, hydroxyl, methoxy or nitro, wherein Hal is fluorine, chlorine, bromine or iodine; thienyl; pyridyl; tetrahydropyranyl; tetrahydrothiopyranyl; and, when at least one of $R^2$, $R^3$, $R^4$, $R^5$ or $R^6$ is other than H, also phenyl; and their physiologically acceptable acid addition salts.

In another process aspect, this invention relates to the use of the novel 1,2,3,4-tetrahydroisoquinolines of this invention as antihelmintics and as intermediates for the production of other anti-helmintics, especially 4-oxo-hexahydropyrazinoisoquinolines of the general Formula II

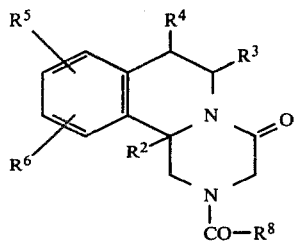

wherein R² to R⁶ and R⁸ have the values given above.

In another composition aspect, this invention relates to pharmaceutical compositions comprising a novel 1,2,3,4-tetrahydroisoquinoline of this invention.

DETAILED DISCUSSION

According to the process of this invention, 1-acylaminomethyl-1,2,3,4-tetrahydroisoquinolines, especially those of the Formula I wherein R⁷=H, are prepared in high yield from the corresponding 1-aminomethyl-1,2,3,4-tetrahydroisoquinolines unsubstituted in the 2-position, especially those of the general Formula III

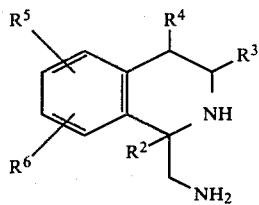

wherein R² to R⁶ have the values given above, by selective acylation on the primary amino group, more particularly by acylating a mono-acid-addition salt thereof with a reactive derivative of a carboxylic acid, especially a compound of the general Formula IV

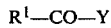

R¹—CO—Y         IV wherein Y is Hal or —O—CO—R¹, wherein Hal and R¹ have the values given above.

Under the conditions described in the literature by acylation of 1-aminomethyl-1,2,3,4-tetrahydroisoquinolines, hitherto only diacyl derivatives were obtainable. Thus, the reaction of 1-aminomethyl-TIS with acetic anhydride produces 1-acetamido-methyl-2-acetyl-TIS. See Helv. Chim. Acta, Vol. 22, page 676 (1939). With the use of triethylamine as an adjuvant base, one obtains mixtures of 2-monoacyl and 1,2-diacyl derivatives.

It has now been found that the desired monoacyl compounds, especially those of the Formula I wherein R⁷=H, can be obtained according to the process of the invention, in high yield by employing a mono-acid-addition salt of a starting aminomethyl-1,2,3,4-tetrahydroisoquinoline unsubstituted in the 2-position, especially those of Formula III, and adding a base which is more weakly basic than the end product.

The starting materials of Formula III are obtainable in high yields by hydrogenation of e.g., 1-cyano-2-acetyl- (or -2-propionyl-, -2-benzoyl-, -2-p-methoxybenzoyl-, -2-cinnamoyl-) 1,2-dihydro- (or 1,2,3,4-tetrahydro) isoquinolines on Raney nickel and subsequent hydrolysis. The last mentioned 1-cyano-2-acyl-isoquinolines are, in turn, also easily obtainable. Thus, it is frequently more favorable not to work up directly the reaction mixture obtained upon hydrogenation but instead to convert the reaction product in two stages, via a hydrolysis and subsequently another acylation, into a compound of Formula I wherein R⁷=H.

The two-stage route has the advantage that the laborious and yield-reducing working up of the hydrogenation mixture can be avoided and consequently higher yields are obtained than according to the previously employed process. Thus, one obtains e.g., in the case of the conversion of 1-cyano-2-benzoyl-1,2-dihydroisoquinoline to 2-benzamidomethyl-TIS, by the routes via the process according to this invention, an overall yield of about 74%, whereas according to the prior art process, a maximum of only 50% was obtained. In the case of the corresponding reaction of the 1-cyano-2-cyclohexylcarbonyl-1,2-dihydroisoquinoline, the yields of 2-cyclohexylcarboxamido-1,2,3,4-tetrahydroisoquinoline were, according to the prior art process, even lower.

The synthesis route proceeding via the process of this invention has the further advantage that one can employ readily obtainable and inexpensive starting materials. Thus, the compounds of Formula III can be prepared, e.g., from the corresponding 1-cyano-2-acetyl- (or -2-propionyl-, -2-benzoyl-, -2-p-methoxybenzoyl-, -2-cinnamoyl-)-1,2-dihydroisoquinolines which, in turn, are obtainable according to known methods in high yields.

A further advantage of the process of this invention is that 1-acylaminomethyltetrahydroisoquinolines of Formula I, which are difficult to obtain or cannot be obtained from the corresponding 1-cyano-2-acyl-1,2-dihydroisoquinolines (e.g., the cyclohexylcarbonyl derivatives) are obtainable elegantly by the process of this invention. By means of the process of this invention, acyl derivatives of Formula I, which are not to be obtained by direct routes, since their acyl radical (e.g., the cyclohexencarbonyl or nitrobenzoyl radical) is sensitive to reducing conditions, can be easily prepared.

Furthermore, for the preparation of the 4-oxo-hexahydropyrazinoisoquinolines of Formula II, it is also of importance that the process according to this invention and the subsequent haloacylation can be carried out one after the other without isolation of the intermediate compounds of Formula I wherein R⁷=H. On the contrary, these can be further worked up directly in the reaction mixture in situ to compounds of Formula I wherein R⁷=—CO—CH₂—X.

It has also been found that compounds of Formula I and especially those of Formula Ia possess, with good compatibility, valuable parasitological and pharmacological properties. They are, inter alia, effective an anthelmintics and, in particular, include a broad spectrum of activity against cestodes and trematodes. The compounds of Formula I and Ia are cardiac and circulatory effective and exhibit a specific analgesic action, e.g., in an intravasal pain model on the dog. This activity component is of importance for pain arising from angina pectoris. Furthermore, they exhibit psychotropic and blood-pressure normalizing properties. Therefore, the compounds of Formula I and Ia can be employed as pharmaceuticals in human and/or veterinary medicine, especially for the achievement of anthelmintic effects, as well as favorable cardiac-circulatory effects.

The 1-acylaminomethyl-1,2,3,4-tetrahydroisoquinolines obtainable according to the invention, especially those of Formula I, can also be used as intermediate products for the preparation of pharmaceuticals, e.g., anthelmintically-effective 2-acyl-4-oxo-1,2,3,6,7,11b-hexahydro-4H-pyrazino[2,1-a]isoquinolines. In particular, the compounds of Formula Ia are suitable as intermediate products for the preparation of anthelmintics of Formula II.

The process of this invention for the preparation of 1-acylaminomethyl-1,2,3,4-tetrahydroisoquinolines comprises reacting a monoacid-addition salt of a 1-aminomethyl-1,2,3,4-tetrahydroisoquinoline unsubstituted in the 2-position, in the presence of a weak base, with a reactive derivative of a carboxylic acid.

More particularly, the process of this invention for the preparation of compounds of Formula I comprises acylating in the presence of weak base, a mono-acid-addition salt of a base of Formula III, wherein $R^2$ to $R^6$ have the values given for Formula I, with a compound of Formula IV, wherein Y is Hal or $-O-CO-R^1$ in which $R^1$ and Hal have the values given for Formula I, and optionally thereafter converting, in the product thus-obtained, the $R^1$ group into another $R^1$ group by treatment with a reducing agent, and/or converting the $R^7$ group when it is H into the radical $-CO-CH_2-X$ by reaction with a compound of the general formula $Y-CO-CH_2-X$, wherein X and Y have the values given above, and/or liberating a base of Formula I from one of its acid-addition salts and/or splitting a racemate thus-obtained into its optical isomers.

As intermediate products, the compounds of Formula Ia wherein $R^7=-CO-CH_2-X$ can be converted in one step into the anthelmintically-effective compounds of Formula II employing a cyclizing agent under conditions which split off HX. Examples of suitable cyclizing agents are strong bases, preferably butyl lithium or potassium tert.-butylate, as well as phenyl lithium, sodium hydride and potassium hydride, alcoholates, e.g., sodium or potassium methylate, ethylate, propylate, isopropylate, n-butylate, tert.-butylate, amides, e.g., lithium diisopropylamide or the corresponding sodium or potassium amides. As a rule, the cyclization is conducted in an inert solvent, e.g., benzene, hexane, tert.-butanol, tetrahydrofuran, hexamethylphosphoric acid triamide, dioxan, diethyl ether, dimethyl formamide, dimethyl sulfoxide, sulfolan, acetonitrile, and if desired, under nitrogen. Suitable reaction temperatures are from about $-20°$ to the boiling point of the solvent employed. The reaction usually is completed in about 15 minutes to about 30 hours, and preferably is conducted from 2 to 10 hours.

Specifically contemplated classes of compounds within the scope of Formula Ia are those wherein:

(a) $R^7$ is H;
(b) $R^7$ is $-CO-CH_2-X$, especially $-CO-CH_2Cl$;
(c) at least $R^2$, preferably $R^2$, $R^5$, $R^6$ and one of $R^3$ and $R^4$, and most preferably all of $R^2$ through $R^6$ are H, including those of (a) and (b), above;
(d) $R^8$ is cyclohexyl, including each of (a)-(c), above;
(e) $R^8$ is substituted phenyl, preferably mono-substituted phenyl and most preferably phenyl substituted in the o-position by fluorine or in the m- or p-position by $-NH_2$, HCONH—, $CH_3CONH$—, F, OH or $-NO_2$, including each of (a)-(c), above;
(f) $R^8$ is thienyl, including each of (a)-(c), above;
(g) $R^8$ is pyridyl, including each of (a)-(c), above;
(h) $R^8$ is tetrahydropyranyl, including each of (a)-(c), above;
(i) $R^8$ is tetrahydrothiopyranyl, including each of (a)-(c), above;

(j) the acid addition salts of those of (a)-(i), above, bearing a basic nitrogen atom.

Of the compounds of Formula Ia, preferred are the compounds of Formulae Ib to If which otherwise correspond to those of Formula Ia but wherein:

Ib. $R^2$ through $R^6$ are H, $R^7$ is H or $-CO-CH_2-Cl$, and $R^8$ is cyclohexyl;

Ic. $R^2$ through $R^6$ are H, $R^7$ is H or $-CO-CH_2-Cl$, and $R^8$ is phenyl substituted in the o-position by fluorine or in the m- or p-position by amino, formylamino, acetylamino, fluorine, hydroxyl or nitro;

Id. $R^2$ through $R^6$ are H, $R^7$ is H or $-CO-CH_2-Cl$, and $R^8$ is thienyl, pyridyl, tetrahydropyranyl or tetrahydrothiopyranyl;

Ie. $R^2$, $R^4$, $R^5$ and $R^6$ are H, $R^3$ is $CH_3$, $R^7$ is H or $-CO-CH_2-Cl$, and $R^8$ is cyclohexyl, phenyl, phenyl substituted in the o-position by fluorine or in the m- or p-position by amino, formylamino, acetylamino, fluorine, hydroxyl or nitro, thienyl, pyridyl, tetrahydropyranyl or tetrahydrothiopyranyl;

If. $R^2$, $R^3$, $R^5$ and $R^6$ each are H, $R^4$ is $CH_3$, $R^7$ is H or $-CO-CH_2-Cl$, and $R^8$ is cyclohexyl, phenyl, phenyl substituted in the o-position by fluorine or in the m- or p-position by amino, formylamino, acetylamino, fluorine, hydroxyl or nitro, thienyl, pyridyl, tetrahydropyranyl or tetrahydrothiopyranyl;

and the acid addition salts of each of the above compounds bearing a basic amino nitrogen atom.

Both the racemic compounds of Formula I and their isolated optical isomers are included as compounds of this invention, especially those having the configuration corresponding to laevorotary 2-benzoyl-4-oxo-1,2,3,6,7,11b-hexahydro-4H-pyrazino[2,1-a]isoquinoline.

As stated above, one aspect of this invention relates to the use of the compounds of Formula Ia as intermediates for the synthesis of the anthelmintics of Formula II by the above-described cyclization.

In the above compounds wherein $R^1$ is alkyl, $R^1$ can be, e.g., methyl, ethyl, propyl, isopropyl, n-butyl, isobutyl, sec.-butyl, tert.-butyl, furthermore n-pentyl, 1-methyl-n-butyl, 2-methyl-n-butyl, isopentyl, 1-ethyl-propyl, 1,1-dimethyl-n-propyl, tert.-pentyl, n-hexyl, 1,1-dimethyl-n-butyl, 2,2-dimethyl-n-butyl and isohexyl. Examples of $R^1$ cycloalkyl radicals are preferably cyclohexyl, as well as cyclobutyl, cyclopentyl or cycloheptyl. Examples of $R^1$ cycloalkenyl radicals are cyclobutenyl-1 or -2, cyclopentenyl-1, -2 or -3, cyclohexenyl-1, -2 or -3 and cycloheptenyl-1, -2, -3 or -4. When $R^1$ is methylcycloalkyl, 2-, 3- or 4-methylcyclohexyl is preferred but other examples are 2- or 3-methylcyclobutyl, 2- or 3-methylcyclopentyl, 1-methylcyclohexyl and 2-, 3- or 4-methylcycloheptyl. When $R^1$ is hydroxycycloalkyl, $R^1$ preferably is 2-, 3- or 4-hydroxycyclohexyl, but can also be 2- or 3-hydroxycyclobutyl, 2- or 3-hydroxycyclopentyl and 2-, 3- or 4-hydroxycycloheptyl. When $R^1$ is oxocycloalkyl, $R^1$ preferably is 3-oxo-cyclopentyl or 4-oxo-cyclohexyl, but can also be 2- or 3-oxocyclobutyl, 2-oxo-cyclopentyl, 2- or 3-oxocyclohexyl or 2-, 3- or 4-oxo-cycloheptyl. When $R^1$ is substituted phenyl, $R^1$ preferably is 3- or 4-aminophenyl, 3- or 4-formylaminophenyl, 3- or 4-acetylaminophenyl, 2-, 3- or 4-fluorophenyl, 3-chlorophenyl, 4-hydroxyphenyl or 3- or 4-nitrophenyl; but can also be, e.g., 2-aminophenyl, 2-formylaminophenyl, 2-acetylaminophenyl, 2- or 4-chlorophenyl, 2-, 3- or 4-bromophenyl, 2-, 3- or 4-iodophenyl, 2,4-, 3,4- or 3,5-difluorophenyl, 2,4-, 3,4- or 3,5-dichlorophenyl, 2,4-dibromophenyl, 2- or 3-hydroxy phenyl, 2-, 3- or 4-methoxyphenyl, 2,4-, 3,4- or 3,5-dimethoxyphenyl, 2,4,6- or 3,4,5-trimethoxyphenyl or 2-nitrophenyl. $R^1$ can also be a heterocyclic radical, preferably thienyl-2 or -3, pyridyl-3, tetrahydropyranyl-4 or tetrahydrothiopyranyl-4, as well as pyridyl-2 or -4, tetrahydropyranyl-2 or -3 or tetrahydrothiopyranyl-2 or -3.

At least one and preferably all of $R^2$, $R^5$ and/or $R^6$ are H, X and Y preferably are chlorine and Hal preferably is fluorine or chlorine. In the compounds of the general formula Y—CO—CH$_2$—X, X and Y are preferably the same.

$R^8$ can have all the values of $R^1$ except (a) alkyl of 1–6 carbon atoms, (b) phenyl trisubstituted by amino, acylamino of up to 4 carbon atoms, hydroxyl, methoxy or nitro, and (c) when $R^2$ through $R^6$ are H, unsubstituted phenyl.

The preparation of the starting compounds especially those of Formula III and also the conversion of compounds of Formula I (obtained according to the process of this invention) into other compounds of Formula I takes place according to methods known per se, such as are described in the literature (e.g., in the standard works, such as Houben-Weyl, Mehoden der organischen Chemie, Georg-Thieme-Verlag, Stuttgart), namely under the reaction conditions known and suitable for the individual reactions.

All starting materials for carrying out of the process according to this invention can, if desired, be formed in situ in such a manner that one does not isolate them from the reaction mixture but instead reacts them in situ.

As starting compounds, there are employed those salts of 1-aminomethyl-1,2,3,4-tetrahydroisoquinolines unsubstituted in the 2-position, especially salts of bases of Formula III, which, per mol of organic base, contain 1 equivalent of acid, i.e., salts in which an amino group is still free (=monoacid addition salts). Thus, in these starting materials, only the ring nitrogen, i.e., the N-atom which is present in the form of a secondary amino group, is bound in salt form. The monoacid addition salts can be prepared, e.g., from the di-salts, especially those of the compounds of Formula III, in situ by adding a chemical equivalent of base to the reaction mixture. The base can be added in solution, e.g., in an aqueous solution, or in solid form, e.g., potassium or sodium hydroxide in pellet form. On the other hand, one can also start from 1-aminomethyltetrahydroisoquinolines in free base form, e.g., from the bases of Formula III, and convert them in situ into monosalts by the addition of a chemical equivalent of acid, into their monosalts. Instead of the acid, for this purpose there can also be employed a corresponding amount of a salt, the cation of which is more weakly basic than the nitrogen atom of the ring system of the 1-aminomethyltetrahydroisoquinoline, especially those of Formula III, e.g., pyridine hydrochloride.

Preferred as anions for the monoacid addition salt are anions of strong inorganic or organic acids, preferably chloride or sulfate. Others which can be employed include fluoride, bromide, iodide, phosphate, perchlorate and the anions of organic sulfonic acids, e.g., methane-, benzene-, p-toluene- or 1- or 2-naphthalene-sulfonic acids.

The reaction of the monoacid addition salts, e.g., a monosalt of a base of Formula III, with a compound of Formula IV is carried out in the presence of a base which is more weakly basic than the reaction product in order that the monoacid addition salt remains and thus the ring nitrogen atom is protected against an acylation. Examples of suitable bases are organic bases, preferably tertiary amines, e.g., pyridine, as well as quinoline, isoquinoline, 5-methylquinoline, acridine, dimethylaniline, p-anisidine, benzimidazole and phenanthridine. It is expedient to use the weak base in about equimolar amounts or in slight excess. The reaction can be carried out in the presence of an inert solvent, preferably acetonitrile or dimethyl formamide, as well as dioxane, tetrahydrofuran and sulfolane.

Preferably, monoacid addition salt, dissolved in one of the above-mentioned solvents, is mixed with 1 molar equivalent of pyridine and 1 molar equivalent of aqueous hydrochloric acid and thereafter a small excess of the reactive derivative of a carboxylic acid, especially of a compound of Formula IV, is added thereto. However, the reaction can also be conducted water-free, e.g., by mixing the solution of the free 1-aminomethyl-1,2,3,4-tetrahydroisoquinoline, especially of the free base of Formula III, in one of the above-mentioned solvents with 1 molar equivalent of pyridine hydrochloride. In both cases, it is preferred to conduct the reaction in a homogeneous phase in order that the chemical equilibrium can be adjusted. The reaction is carried out at temperatures of about 0° to 100°, preferably at about room temperature. Accordingly, the reaction times vary from about 0.5 to 24 hours, preferably from 2 to 4 hours.

The $R^1$ group of a thus-obtained compound of Formula I can be converted, according to methods described in the literature, with a reducing agent into another $R^1$ group.

Thus, it is possible to reduce a nitro group in $R^1$ to an amino group, expediently by catalytic hydrogenation or by chemical means. As catalysts for the catalytic hydrogenation, the usual catalysts known from the literature, preferably the noble metal but also copper-chromium oxide as well as nickel and cobalt catalysts, can be employed. The noble metal catalysts can be employed, for example, as carrier catalysts (e.g., palladium or charcoal), as oxide catalysts (e.g., platinum oxide) or as finely divided metal catalysts (e.g., platinum black). Nickel and cobalt catalysts are expediently used as Raney metals. Nickel can also be employed on kieselguhr or pumice as carrier. The hydrogenation can be carried out at pressures of about 1 to 200 atms. and at temperatures from about 0° to 200°, depending on the catalyst employed and the group to be reduced, expediently in the presence of a solvent, preferably an alcohol, e.g., methanol, ethanol, isopropanol or tert.-butanol, or ethyl acetate, or an ether, e.g., dioxane or tetrahydrofuran, or water and/or an aqueous solution of an alkali metal hydroxide. For the reduction of a nitro group, metals, e.g., iron, zinc, and acids, e.g., HCl, CH$_3$COOH, or salts, e.g., tin(II) chloride or titanium(III) chloride, can be employed.

A keto group in $R^1$ can be converted by hydrogenation or by chemical means into a hydroxyl group. For this hydrogenation, the above-mentioned methods preferably are employed. Furthermore, the keto group can be reduced with nascent hydrogen, e.g., by treat with zinc/acid or zinc/aqueous alkali metal hydroxide solution. As acid, acetic acid, e.g., is suitable. Sodium or another alkali metal in a lower alcohol, e.g., ethanol, isopropanol or isoamyl alcohol, can also be used. The keto group can also be reduced with metal hydrides. Complex metal hydrides are preferred which do not attack the acid amide group, e.g., sodium borohydride, lithium borohydride, potassium tri(sec.-butyl) borohydride, potassium trimethoxyborohydride, expediently in an inert solvent, e.g., of an ether, such as for example, diethyl ether, tetrahydrofuran, dioxane, 1,2-dimethoxyethane or diglyme. Sodium borohydride can also be used in aqueous or aqueous-alcoholic solution. The reaction occurs from about −80° to +100°, especially −20° to the boiling point of the solvent used.

A keto group can also be converted into a methylene group by reaction with hydrazine and subsequent decomposition of the hydrazone formed according to the method of Wolff-Kishner.

Under the above-described conditions, a double bond, e.g., $R^1$=cycloalkenyl, can be hydrogenated to a single bond, preferably by catalytic hydrogenation, e.g., on $PtO_2$, palladium or Raney nickel.

In a product thus-obtained of Formula I, the $R^7$ hydrogen atom can be converted, according to methods known per se by reaction with a compound of the general formula Y—CO—$CH_2$—X, into a radical wherein $R^7$=—CO—$CH_2$X. This reaction is expediently carried out in an inert solvent in the presence of an inorganic or organic base. As suitable inert solvents, preferred are methylene chloride and acetonitrile. Others which can be used include aromatic hydrocarbons, e.g., benzene, substituted aromatic hydrocarbons, e.g., xylene, toluene, chlorobenzene or nitrobenzene and chlorinated alkanes, e.g., chloroform, carbon tetrachloride or tetrachloroethane. Inorganic bases are preferably employed, e.g., triethylamine or pyridine. However, other organic bases, e.g., quinoline, isoquinoline and inorganic bases, e.g., sodium carbonate, potassium carbonate, sodium bicarbonate, potassium bicarbonate, aqueous sodium hydroxide solution or aqueous potassium hydroxide solution, are also suitable. The reaction occurs at temperatures of about 0° to 150°, preferably from about 20° to 50°. Correspondingly, the reaction is complete in about 5-24 hours, usually about 2 to 4 hours.

Compounds of Formula I which contain a basic substituent can be converted, by treatment with an acid, into their acid addition salts, e.g., into their hydrochlorides, sulfates, citrates or methane-sulfonates.

The compounds of Formula I contain at least one center of asymmetry and can, therefore, be present in racemic or in optically-active form. Expediently, optically-active compounds of Formula I are obtained employing starting materials of Formulae III or IV which are optically active. It is also possible to separate racemates of Formula I ($R^7$=H) into their optical antipodes, preferably by chemical methods. Thus, in the usual way, one can, e.g., separate racemates of Formula I ($R^7$=H) employing optically-active acids. As such, there are e.g. suitable the (+)- and (−)-forms of tartaric acid, dibenzoyltartaric acid, diacetyltartaric acid, campheric acid, β-camphorsulfonic acid, mandelic acid, malic acid, 2-phenylbutyric acid, dinitrodiphenic acid, lactic acid or quinic acid.

The starting compounds of Formulae III and IV are known or can be prepared in analogy to known compounds according to standard processes. Thus, e.g., the compounds of Formula III in which $R^2$ to $R^6$ are other than H are obtainable from the correspondingly substituted 1-cyano-2-acyl-1,2-dihydro- or -1,2,3,4-tetrahydroisoquinolines, wherein the acyl group preferably is acetyl, propionyl or benzoyl. These can be hydrogenated on Raney nickel at elevated temperatures and pressures and the hydrogenation mixture converted in per se known manner, by hydrolysis, into the corresponding 1-aminomethyl-1,2,3,4-tetrahydroisoquinolines of Formula III.

Compounds of formula III wherein $R^2$=$CH_3$ are obtainable from the corresponding 1-cyano-2-acyl-1,2-dihydro- or -1,2,3,4-tetrahydroisoquinolines by methylation in the 1-position, hydrogenation on Raney nickel and subsequent hydrolysis.

The compounds of Formula Ia and their acid addition salts are excellently effective against cestodes and trematodes. They can, e.g., be employed against the following cestodes (arranged according to hosts):

1. Ruminants: Moniezia, Stilesia, Avitellina, Thysanosoma, Thysaniezia, hydatids of Taenia sp., *Coenurus cerebralis, Echinococcus hydatids;* 2. Ungulates: Anoplocephala; 3. Rodents: Hymenolepis (especially *H. nana* and *H. diminuta*); 4. Birds: Davainea, Raillietina, Hymenolepis; Canines and felines: Taenia (especially *T. hydatigena, T. pisiformis, T. taeniaeformis, T. ovis, T. serialis, T. cervi, T. multiceps*), Dipylidium (especially *D. caninum*), Echinococcus (especially *E. granulosus* and *E. multilocularis*); 6 Humans: Taenia (especially *T. solium, T. saginata, T. serialis*), Hymenolepis (especially *H. nana* and *H. diminuta*), Drepanidotaenia, Dipylidium, Diplopylidium, Coenurus (especially *C. cerebralis*), Diphyllobothrium (especially *D. latum*), Echinococcus hydatids (especially of *E. granulosus* and *E. multilocularis*). Among the important trematodes in human and veterinary medicine, of primary importance is the use of the compounds combating those of the family Schistosoma (*Sch. mansoni, Sch. haematobium, Sch. japonicum*).

The compounds of Formula Ia and their acid addition salts can be employed as such or combined with pharmaceutically acceptable inert carriers as medicines in human and veterinary medicine. Carriers of this type can, e.g., be in the form of capsules, solid dilution agents or filling materials, sterile aqueous media and/or nontoxic organic solvents.

As forms of administration, suitable are, e.g., tablets and dragees, effervescent tablets, capsules, granulates, aqueous suspensions, injectable solutions, emulsions and suspensions, elixirs, syrups or pastes. The formulations for this purpose are prepared in known manner, e.g., by addition of the active materials to solvents and/or carrier materials. The compounds of Formula Ia and their acid addition salts can also be present in the formulations in admixture with other active materials.

The administration of the active materials of Formula Ia and their acid addition salts preferably is oral. However, a parenteral or dermal administration is also possible. The compounds are preferably administered in dosages of about 0.01 to 2500 mg. per dosage unit. The daily dosage preferably is from 0.01 to 250, especially from 0.5 to 100 mg./kg. body weight.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following Examples, [α] means $[\alpha]_D^{20}$ in chloroform. Temperatures are in degrees Celsius.

EXAMPLE 1

To a solution of 48.6 g. 1-aminomethyl-TIS (1-aminomethyl-1,2,3,4-tetrahydroisoquinoline) in 600 ml. acetonitrile is added 26 g. pyridine and 151 ml. HCl.

48.4 g. cyclohexanecarboxylic acid chloride in 200 ml. acetonitrile is then added dropwise and the mixture is stirred for two hours at 20°. The reaction mixture is concentrated, diluted with diethyl ether and extracted with 1 N hydrochloric acid. The extract is rendered alkaline with aqueous sodium hydroxide solution and extracted with chloroform. After drying with magnesium sulfate and evaporation of the chloroform, there is obtained 1-cyclohexy carboxamidomethyl-TIS; m.p. 107°–108° (from acetone/petroleum ether).

EXAMPLES 2 to 88

Analogously to Example 1, from 1-aminomethyl-TIS monohydrochloride and the corresponding carboxylic acid chlorides, there is obtained the following compounds:

2. 1-acetamidomethyl-TIS; m.p. 87°
3. 1-propionamidomethyl-TIS
4. 1-n-butyramidomethyl-TIS
5. 1-isobutyramidomethyl-TIS
6a. 1-n-pentanoylaminomethyl-TIS
6b. 1-trimethylacetamidomethyl-TIS
7. 1-n-hexanoylaminomethyl-TIS
8. 1-cyclobutylcarboxamidomethyl-TIS
9. 1-cyclopentylcarboxamidomethyl-TIS
10. 1-cycloheptylcarboxamidomethyl-TIS
11. 1-(3-cyclohexenylcarboxamidomethyl)-TIS; m.p. 98°
12. 1-(2-methylcyclopentylcarboxamidomethyl)-TIS
13. 1-(3-methylcyclopentylcarboxamidomethyl)-TIS
14. 1-(1-methylcyclohexylcarboxamidomethyl)-TIS
15. 1-(2-methylcyclohexylcarboxamidomethyl)-TIS
16. 1-(3-methylcyclohexylcarboxamidomethyl)-TIS
17. 1-(4-methylcyclohexylcarboxamidomethyl)-TIS
18. 1-(2-hydroxycyclopentylcarboxamidomethyl)-TIS
19. 1-(3-hydroxycyclopentylcarboxamidomethyl)-TIS
20. 1-(2-hydroxycyclohexylcarboxamidomethyl)-TIS
21. 1-(3-hydroxycyclohexylcarboxamidomethyl)-TIS
22. 1-(4-hydroxycyclohexylcarboxamidomethyl)-TIS
23. 1-(2-oxocyclopentylcarboxamidomethyl)-TIS
24. 1-(3-oxocyclopentylcarboxamidomethyl)-TIS
25. 1-(2-oxocyclohexylcarboxamidomethyl)-TIS
26. 1-(3-oxocyclohexylcarboxamidomethyl)-TIS
27. 1-(4-oxocyclohexylcarboxamidomethyl)-TIS
28. 1-(2-oxocycloheptylcarboxamidomethyl)-TIS
29. 1-(3-oxocycloheptylcarboxamidomethyl)-TIS
30. 1-(4-oxocycloheptylcarboxamidomethyl)-TIS
31. 1-cyclohexylcarboxamidomethyl-1-methyl-TIS; m.p. 105°
32a. 1-cyclohexylcarboxamidomethyl-3-cis-methyl-TIS
32b. 1-cyclohexylcarboxamidomethyl-3-trans-methyl-TIS
33. 1-cyclohexylcarboxamidomethyl-4-methyl-TIS
34. 1-cyclohexylcarboxamidomethyl-5-methyl-TIS
35. 1-cyclohexylcarboxamidomethyl-6-methyl-TIS
36. 1-cyclohexylcarboxamidomethyl-7-methyl-TIS
37. 1-cyclohexylcarboxamidomethyl-8-methyl-TIS
38. 1-benzamidomethyl-TIS; m.p. 127°
39. 1-benzamidomethyl-1-methyl-TIS
40. 1-benzamidomethyl-3-cis-methyl-TIS; m.p. 129°
41. 1-benzamidomethyl-3-trans-methyl-TIS
42. 1-benzamidomethyl-4-methyl-TIS
43. 1-benzamidomethyl-5-methyl-TIS
44. 1-benzamidomethyl-6-methyl-TIS
45. 1-benzamidomethyl-7-methyl-TIS
46. 1-benzamidomethyl-8-methyl-TIS
47. 1-benzamidomethyl-6,7-dimethyl-TIS
48. 1-benzamidomethyl-5-methoxy-TIS
49. 1-benzamidomethyl-6-methoxy-TIS
50. 1-benzamidomethyl-7-methoxy-TIS
51. 1-benzamidomethyl-8-methoxy-TIS
52. 1-benzamidomethyl-6,7-dimethoxy-TIS; m.p. 122°
53. 1-(2-fluorobenzamidomethyl)-TIS
54. 1-(3-fluorobenzamidomethyl)-TIS
55. 1-(4-fluorobenzamidomethyl)-TIS; m.p. 127°–129°
56. 1-(2-chlorobenzamidomethyl)-TIS
57. 1-(3-chlorobenzamidomethyl)-TIS
58. 1-(4-chlorobenzamidomethyl)-TIS
59. 1-(4-bromobenzamidomethyl)-TIS
60. 1-(4-iodobenzamidomethyl))-TIS
61. 1-(2-nitrobenzamidomethyl)-TIS
62. 1-(3-nitrobenzamidomethyl)-TIS
63. 1-(4-nitrobenzamidomethyl)-TIS; m.p. 150°–151°
64. 1-(2-formylaminobenzamidomethyl)-TIS
65. 1-(3-formylaminobenzamidomethyl)-TIS
66. 1-(4-formylaminobenzamidomethyl)-TIS
67. 1-(2-acetylaminobenzamidomethyl)-TIS
68. 1-(3-acetylaminobenzamidomethy)-TIS.
69. 1-(4-acetylaminobenzamidomethyl)-TIS.
70. 1-(2-methoxybenzamidomethyl)-TIS
71. 1-(3-methoxybenzamidomethyl)-TIS
72. 1-(4-methoxybenzamidomethyl)-TIS
73. 1-(2,4-dimethoxybenzamidomethyl)-TIS
74. 1-(3,4-dimethoxybenzamidomethyl)-TIS
75. 1-(3,5-dimethoxybenzamidomethyl)-TIS
76. 1-(2,4,6-trimethoxybenzamidomethyl)-TIS
77. 1-(3,4,5-trimethoxybenzamidomethyl)-TIS
78. 1-(thienyl-2-carboxamidomethyl)-TIS
79. 1-(thienyl-3-carboxamidomethyl)-TIS
80. 1-(pyridyl-2-carboxyamidomethyl)-TIS
81. 1-(pyridyl-3-carboxamidomethyl)-TIS
82. 1-(pyridyl-4-carboxamidomethyl)-TIS
83. 1-(tetrahydropyranyl-2-carboxamidomethyl)-TIS
84. 1-(tetrahydropyranyl-3-carboxamidomethyl)-TIS
85. 1-(tetrahydropyranyl-4-carboxamidomethyl)-TIS; m.p. 130°–131°
86. 1-(tetrahydrothiopyranyl-2-carboxamidomethyl)-TIS
87. 1-(tetrahydrothiopyranyl-3-carboxamidomethyl)-TIS
88. 1-(tetrahydrothiopyranyl-4-carboxamidomethyl)-TIS.

EXAMPLE 89

157 ml. 2 N aqueous sodium hydroxide solution and 29.8 g. pyridine are added to 73.8 g. 1-aminomethyl-TIS dihydrochloride suspended in 600 ml. acetonitrile.

To this mixture is added dropwise, over the course of an hour, 55.3 g. cyclohexane-carboxylic acid chloride in 250 ml. acetonitrile (exothermal reaction) and the mixture is stirred for 3 hours. Substantially all of the acetonitrile is evaporated, the residue is mixed with 1 liter of water and the solution made weakly acidic with 25% hydrochloric acid. For purification, the aqueous solution is extracted with toluene, rendered alkaline with aqueous sodium hydroxide solution and extracted with methylene chloride. The methylene chloride extract is dried over magnesium sulfate and evaporated to give 1-cyclohexylcarboxamidomethyl-TIS; m.p. 107°–108° (from acetone).

The compounds of Examples 2 to 88 can be obtained analogously by acylation. For example, 1-cyclohexyl-carboxamidomethyl-1-methyl-TIS (m.p. 105°) is obtained by reaction of cyclohexane-carboxylic acid chloride with 1-aminomethyl-1-methyl-TIS dihydrochloride (m.p. 290°; obtained from 1-methyl-2-benzoyl-1,2- dihydroisoquinoline-1-cyanide by hydrogenation in the presence of Raney nickel and subsequent hydrolysis with hydrochloric acid).

EXAMPLE 90

To 48.6 g. 1-aminomethyl-TIS and 35 g. pyridine hydrochloride in 1000 ml. dimethylformamide is added 44 g. cyclohexane-carboxylic acid chloride in 200 ml. dimethylformamide. After stirring for two hours at 20°, the reaction mixture is mixed with diethyl ether and extracted with dilute hydrochloric acid. The aqueous phase is rendered alkaline with aqueous sodium hydroxide solution and extracted with chloroform. After drying over magnesium sulfate and evaporation of the solvent, there is obtained 1-cyclohexylcarboxamidomethyl-TIS; m.p. 107°–108° (from acetone/petroleum ether).

Analogously, (+)-1-cyclohexylcarboxamidomethyl-TIS, m.p. 107°; $[\alpha] = +5.3°$ (in ethanol), is obtained from (+)-1-aminomethyl-TIS (hydrochloride, m.p. 212°; $[\alpha]_{405}^{20} = +10.9°$ (in water); prepared from racemic 1-aminomethyl-TIS by racemate separation with tartaric acid. Corresponding, (−)-1-cyclohexylcarboxamidomethyl-TIS, m.p. 107°, $[\alpha] -5.2°$ (in ethanol), is obtained from (−)-1-aminomethyl-TIS.

EXAMPLE 91

To 21.7 g. 1-cyclohexylcarboxamidomethyl-TIS, prepared according to Example 1, in 300 ml. methanol, is added a solution of 16.5 g. L(+)-tartaric acid in 300 ml. methanol. The solvent is distilled off, and the residue from ethanol recrystallized until the m.p. has increased to about 207°. The salt is dissolved in water, the solution rendered alkaline and then extracted with chloroform. After drying over magnesium sulfate and distilling off of the solvent, there is obtained (+)-1-cyclohexylcarboxamidomethyl-TIS; m.p. 107° (from acetone/petroleum ether), $[\alpha] = +5.3$ (in ethanol).

Analogously, with D(−)-tartaric acid, there is obtained (−)-1-cyclohexylcarboxamidomethyl-TIS, m.p. 107°; $[\alpha] = -5.2°$.

(−)-1-Benzamidomethyl-TIS, m.p. 129°; $[\alpha] = -25.8°$, is obtained analogously from 1-benzamidomethyl-TIS and L(+)-tartaric acid, and from the same starting material and D(−)-tartaric acid, (+)-1-benzamidomethyl-TIS, m.p. 129°; $[\alpha] = +27.0°$, is obtained.

27 g. 1-(3-cyclohexenyl-carboxamidomethyl)-TIS in 200 ml. methanol are hydrogenated in the presence of 0.5 g. PtO$_2$ at 20° and normal pressure. After evaporation of the solvent, there is obtained 1-cyclohexylcarboxamidomethyl-TIS; m.p. 107°–108° (from diethyl ether).

EXAMPLE 93

A solution of 67 g. 1-(4-nitrobenzamidomethyl)-TIS in 1,500 ml. methanol is hydrogenated on 12 g. 5% palladium charcoal at 20° under normal pressure. The catalyst is filtered off and the filtrate evaporated. From the residue, there is obtained 1-(4-aminobenzamidomethyl)-TIS; m.p. 163°–164°; hydrochloride m.p. 185°–196° (decomposition).

EXAMPLES 94 to 98

Analogously to Example 93, the following compounds are obtained from the corresponding nitro compounds:
94. 1-(2-aminobenzamidomethyl)-TIS
95. 1-(-aminobenzamidomethyl)-TIS
96. 1-(2-aminobenzamidomethyl)-2-chloroacetyl-TIS
97. 1-(3-aminobenzamidomethyl)-2-chloroacetyl-TIS
98. 1-(4-aminobenzamidomethyl)-2-chloroacetyl-TIS

EXAMPLE 99

(a) To 6 g. 1-(4-oxocyclohexylcarboxamidomethyl)-TIS in 100 ml. ethanol, 1.15 g. sodium borohydride is added portionwise at 0°. The mixture is stirred for 12 hours at 20° and poured onto ice to give 1-(4-hydroxycyclohexylcarboxamidomethyl)-TIS.

(b) 6 g. 1-(4-oxocyclohexylcarboxamidomethyl)-TIS in 100 ml. methanol is hydrogenated in the presence of 2 g. Raney nickel at 50° and 100 atms. up to saturation. The catalyst is then filtered off to obtain, after evaporation of the solvent, 1-(4-hydroxycyclohexylcarboxamidomethyl)-TIS.

EXAMPLES 100 to 108

Analogously to Examples 99(a) and (b), the following compounds can be obtained from the corresponding oxo compounds by reduction:
100. 1-(2-hydroxycyclopentylcarboxamidomethyl)-TIS
101. 1-(3-hydroxycyclopentylcarboxamidomethyl)-TIS
102. 1-(2-hydroxycyclohexylcarboxamidomethyl)-TIS
103. 1-(3-hydroxycyclohexylcarboxamidomethyl)-TIS
104. 1-(2-hydroxycyclopentylcarboxamidomethyl)-2-chloroacetyl-TIS
105. 1-(3-hydroxycyclopentylcarboxamidomethyl)-2-chloroacetyl-TIS
106. 1-(2-hydroxycyclohexylcarboxamidomethyl)-2-chloroacetyl-TIS
107. 1-(3-hydroxycyclohexylcarboxamidomethyl)-2-chloroacetyl-TIS
108. 1-(4-hydroxycyclohexylcarboxamidomethyl)-2-chloroacetyl-TIS

EXAMPLE 109

To a solution of 136 g. 1-cyclohexylcarboxamidomethyl-TIS and 60.6 g triethylamine in 1,500 ml. methylene chloride is added 62.5 g. chloroacetyl chloride in 1,500 ml. methylene chloride. The mixture is boiled for three hours, then shaken with dilute hydrochloric acid and water and dried over magnesium sulfate. After evaporation of the solvent, there is obtained 1-cyclohexylcarboxamidomethyl-2-chloroacetyl-TIS; m.p. 151°–152° (from ethanol/diethyl ether).

EXAMPLES 110 to 190

Analogous to Example 109, from the acylated 1-aminomethyl-tetrahydroisoquinolines of Examples 1 to 82, there is obtained, by reaction with chloroacetyl chloride, the following compounds:
110. (+)-1-cyclohexylcarboxamidomethyl-2-chloroacetyl-TIS, m.p. 142°; $[\alpha] = +89.5°$ (from (−)-1-cyclohexylcarboxamidomethyl-TIS)
111. (−)-1-cyclohexylcarboxamidomethyl-2-chloroacetyl-TIS of m.p. 142°; $[\alpha] = -89.3°$ (from (+)-1-cyclohexylcarboxamidomethyl-TIS)
112. 1-acetamidomethyl-2-chloroacetyl-TIS, m.p. 159°–161°
113. 1-propionamidomethyl-2-chloroacetyl-TIS
114. 1-n-butyramidomethyl-2-chloroacetyl-TIS
115. 1-isobutyramidomethyl-2-chloroacetyl-TIS
116. 1-n-pentanoylaminomethyl-2-chloroacetyl-TIS
117. 1-trimethylacetamidomethyl-2-chloroacetyl-TIS
118. 1-n-hexanoylaminomethyl-2chloroacetyl-TIS
119. 1-cyclobutylcarboxamidomethyl-2-chloroacetyl-TIS 120. 1-cyclopentylcarboxamidomethyl-2-chloroacetyl-TIS
121. 1-cycloheptylcarboxamidomethyl-2-chloroacetyl-TIS
122. 1-(3-cyclohexenyl-carboxamidomethyl)-2-chloroacetyl-TIS of m.p. 144°–145° (from 1-(3-cyclohexenylcarboxamidomethyl)-TIS
123. 1-(2-methylcyclopentylcarboxamidomethyl)-2-chloroacetyl-TIS
124. 1-(3-methylcyclopentylcarboxamidomethyl)-2-chloroacetyl-TIS
125. 1-(1-methylcyclohexylcarboxamidomethyl)-2-chloroacetyl-TIS
126. 1-(2-methylcyclohexylcarboxamidomethyl)-2-chloroacetyl-TIS
127. 1-(3-methylcyclohexylcarboxamidomethyl)-2-chloroacetyl-TIS
128. 1-(4-methylcyclohexylcarboxamidomethyl)-2-chloroacetyl-TIS
129. 1-(2-oxocyclopentylcarboxamidomethyl)-2-chloroacetyl-TIS
130. 1-(3-oxocyclopentylcarboxamidomethyl)-2-chloroacetyl-TIS
131. 1-(2-oxocyclohexylcarboxamidomethyl)-2-chloroacetyl-TIS
132. 1-(3-oxocyclohexylcarboxamidomethyl)-2-chloroacetyl-TIS
133. 1-(4-oxocyclohexylcarboxamidomethyl)-2-chloroacetyl-TIS
134. 1-(2-oxocycloheptylcarboxamidomethyl)-2-chloroacetyl-TIS
135. 1-(3-oxocycloheptylcarboxamidomethyl)-2-chloroacetyl-TIS
136. 1-(4-oxocycloheptylcarboxamidomethyl)-2-chloroacetyl-TIS
137. 1-cyclohexylcarboxamidomethyl-1-methyl-2-chloroacetyl-TIS; m.p. 120°–121°
138a. 1-cyclohexylcarboxamidomethyl-2-chloroacetyl-3-cis-methyl-TIS
138b. 1-cyclohexylcarboxamidomethyl-2-chloroacetyl-3-trans-methyl-TIS
139a. 1-cyclohexylcarboxamidomethyl-2-chloroacetyl-4-methyl-TIS
139b. 1-cyclohexylcarboxamidomethyl-2-chloroacetyl-5-methyl-TIS
139c. 1-cyclohexylcarboxamidomethyl-2-chloroacetyl-6-methyl-TIS
139d. 1-cyclohexylcarboxamidomethyl-2-chloroacetyl-7-methyl-TIS
139e. 1-cyclohexylcarboxamidomethyl-2-chloroacetyl-8-methyl-TIS
140. 1-benzamidomethyl-2-chloroacetyl-TIS; m.p. 175°
141. 1-benzamidomethyl-1-methyl-2-chloroacetyl-TIS
142. 1-benzamidomethyl-2-chloroacetyl-3-cis-methyl-TIS, m.p. 140°
143. 1-benzamidomethyl-2-chloroacetyl-3-trans-methyl-TIS
144. 1-benzamidomethyl-2-chloroacetyl-4-methyl-TIS, m.p. 185°–186°
145. 1-benzamidomethyl-2-chloroacetyl-5-methyl-TIS
146. 1-benzamidomethyl-2-chloroacetyl-6-methyl-TIS
147. 1-benzamidomethyl-2-chloroacetyl-7-methyl-TIS
148. 1-benzamidomethyl-2-chloroacetyl-8-methyl-TIS
149. 1-benzamidomethyl-2-chloroacetyl-6,7-dimethyl-TIS
150. 1-benzamidomethyl-2-chloroacetyl-5-methoxy-TIS
151. 1-benzamidomethyl-2-chloroacetyl-6-methoxy-TIS
152. 1-benzamidomethyl-2-chloroacetyl-7-methoxy-TIS
153. 1-benzamidomethyl-2-chloroacetyl-8-methoxy-TIS
154. 1-benzamidomethyl-2-chloroacetyl-6,7-dimethoxy-TIS, m.p. 176°
155. 1-(2-fluorobenzamidomethyl)-2-chloroacetyl-TIS
156. 1-(3-fluorobenzamidomethyl)-2-chloroacetyl-TIS
157. 1-(4-fluorobenzamidomethyl)-2-chloroacetyl-TIS
158. 1-(2-chlorobenzamidomethyl)-2-chloroacetyl-TIS
159. 1-(3-chlorobenzamidomethyl)-2-chloroacetyl-TIS
160. 1-(4-chlorobenzamidomethyl)-2-chloroacetyl-TIS
161. 1-(4-bromobenzamidomethyl)-2-chloroacetyl-TIS
162. 1-(4-iodobenzamidomethyl)-2-chloroacetyl-TIS
163. 1-(2-nitrobenzamidomethyl)-2-chloroacetyl-TIS
164. 1-(3-nitrobenzamidomethyl)-2-chloroacetyl-TIS
165. 1-(4-nitrobenzamidomethyl)-2-chloroacetyl-TIS
166. 1-(2-formylaminobenzamidomethyl)-2-chloroacetyl-TIS
167. 1-(3-formylaminobenzamidomethyl)-2-chloroacetyl-TIS
168. 1-(4-formylaminobenzamidomethyl)-2-chloroacetyl-TIS
169. 1-(2-acetylaminobenzamidomethyl)-2-chloroacetyl-TIS
170. 1-(3-acetylaminobenzamidomethyl)-2-chloroacetyl-TIS
171. 1-(4-acetylaminobenzamidomethyl)-2-chloroacetyl-TIS
172. 1-(2-methoxybenzamidomethyl)-2-chloroacetyl-TIS
173. 1-(3-methoxybenzamidomethyl)-2-chloroacetyl-TIS
174. 1-(4-methoxybenzamidomethyl)-2-chloroacetyl-TIS
175. 1-(2,4-dimethoxybenzamidomethyl)-2-chloroacetyl-TIS
176. 1-(3,4-dimethoxybenzamidomethyl)-2-chloroacetyl-TIS
177. 1-(3,5-dimethoxybenzamidomethyl)-2-chloroacetyl-TIS
178. 1-(2,4,6-trimethoxybenzamidomethyl)-2-chloroacetyl-TIS
179. 1-(3,4,5-trimethoxybenzamidomethyl)-2-chloroacetyl-TIS
180. 1-(thienyl-2-carboxamidomethyl)-2-chloroacetyl-TIS
181. 1-(thienyl-3-carboxamidomethyl)-2-chloroacetyl-TIS
182. 1-(pyridyl-2-carboxamidomethyl)-2-chloroacetyl-TIS
183. 1-(pyridyl-3-carboxamidomethyl)-2-chloroacetyl-TIS
184. 1-(pyridyl-4-carboxamidomethyl)-2-chloroacetyl-TIS
185. 1-(tetrahydropyranyl-2-carboxamidomethyl)-2-chloroacetyl-TIS
186. 1-(tetrahydropyranyl-3-carboxamidomethyl)-2-chloroacetyl-TIS
187. 1-(tetrahydropyranyl-4-carboxamidomethyl)-2-chloroacetyl-TIS
188. 1-(tetrahydrothiopyranyl-2-carboxamidomethyl)-2-chloroacetyl-TIS
189. 1-(tetrahydrothiopyranyl-3-carboxamidomethyl)-2-chloroacetyl-TIS 190. 1-(tetrahydrothiopyranyl-4-carboxamidomethyl)-2-chloroacetyl-TIS.

EXAMPLES OF USE

EXAMPLE 191

To 14 g. potassium tert.-butylate in 250 ml. acetonitrile, is added over the course of 15 minutes, a solution of 34.9 g. 1-cyclohexylcarboxamidomethyl-2-chloroacetyl-TIS in 250 ml. acetonitrile. The mixture is stirred for 5 hours, then mixed with water, the solvent evaporated off and the residue taken up in methylene chloride and washed with water. After drying the organic phase over magnesium sulfate and evaporation of the solvent, there is obtained 2-cyclohexylcarbonyl-4-oxo-1,2,3,6,7,11,hexahydro-4H-pyrazino[2,1-a]-isoquinoline; m.p. 137°–138° (from acetone/diethyl ether).

There are obtained analogously: (−)-2-cyclohexylcarbonyl-4-oxo-1,2,3,6,7,11b-hexahydro-4H-pyrazino[2,1-a]isoquinoline, m.p. 107°–108°; [α] = −149.4° (from (−)-1-cyclohexylcarboxamidomethyl-2-chloroacetyl-TIS); (+)-2-cyclohexylcarbonyl-4-oxo-1,2,3,6,7,11b-hexahydro-4H-pyrazino[2,1-a]isoquinoline, m.p. 107°–108°; [α] = +148.2° (from (+)-1-cyclohexylcarboxamidomethyl-2-chloroacetyl-TIS); 2-(3-cyclohexenyl-carbonyl)-4-oxo-1,2,3,6,7,11b-hexahydro-4H-pyrazino[2,1-a]isoquinoline, m.p. 126° (from 1-(3-cyclohexenylcarboxamidomethyl)-2-chloroacetyl-TIS).

EXAMPLE 192

To 1 g. (−)-1-cyclohexylcarboxamidomethyl-2-chloroacetyl-TIS in 50 ml. absolute tetrahydrofuran is added at 20° 1.5 ml. of a 20% butyl lithium solution in hexane. The mixture is stirred for 2 hours at 20°, boiled for 6 hours, hydrolyzed with water and the solvent evaporated off.

The residue is taken up in chloroform and washed with water. After drying over magnesium sulfate and evaporation of the solvent, there is obtained (−)-2-cyclohexylcarbonyl-4-oxo-1,2,3,6,7,11b-hexahydro-4H-pyrazino[2,1-a]isoquinoline, m.p. 107°–108° (from acetone/diethyl ether); [α] = −149.4°.

EXAMPLE 193

39.6 g. 1-cyano-2-acetyl-1,2-dihydroisoquinoline are hydrogenated in 600 ml. ethyl acetate in the presence of 30 g. Raney nickel for 16 hours at 260 atms. and 85°. The solvent is evaporated and the residue boiled for 12 hours in 300 ml. 25% hydrochloric acid. The mixture is then rendered alkaline, extracted with methylene chloride and the organic phase dried over magnesium sulfate. The solvent is stripped off and the residue, consisting of crude 1-aminomethyl-TIS dihydrochloride, is dissolved in 400 ml. acetonitrile and then mixed with 17.4 g. pyridine, 100.4 ml. 2 N hydrochloric acid and 32.3 g. cyclohexane-carboxylic acid chloride in 150 ml. acetonitrile. After 2 hours, the solvent is evaporated off, the residue acidified with dilute hydrochloric acid and extracted with diethyl ether, the aqueous layer made alkaline and then extracted with methylene chloride. After drying over magnesium sulfate, the methylene chloride is evaporated off to give 1-cyclohexylcarboxamidomethyl-TIS; m.p. 107°–108° (from diethyl ether).

EXAMPLE 194

1.62 g. 1-aminomethyl-TIS in 20 ml. acetonitrile are reacted analogously to Example 1 in the presence of 0.87 g. pyridine and 5 ml. 2 N HCl with 1.62 g. cyclohexane-carboxylic acid chloride. After 4 hours, the solution, which contains 1-cyclohexylcarboxamidomethyl-TIS is mixed with 4.8 g. 47% KOH and 2.5 g. chloroacetyl chloride in 10 ml. acetonitrile then added thereto. The mixture is stirred for 4 hours at 20°, the solvent evaporated off, the residue taken up in methylene chloride, the solution shaken successively with dilute hydrochloric acid, dilute aqueous sodium hydroxide solution and water, dried over magnesium sulfate and then evaporated, to obtain 1-cyclohexylcarboxamidomethyl-2-chloroacetyl-TIS; m.p. 151°–152°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a compound of the formula

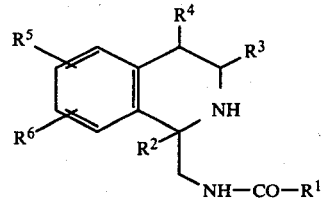

wherein $R^1$ is alkyl of 1–6 carbon atoms; cycloalkyl or cycloalkenyl each having 4–7 ring carbon atoms and the cycloalkyl optionally being substituted by one of methyl, hydroxyl and oxo; phenyl; phenyl substituted by 1–3 amino, carboxylic acylamino of up to 4 carbon atoms, Hal, hydroxyl, methoxy and nitro, wherein Hal is fluorine, chlorine, bromine or iodine; thienyl; pyridyl; tetrahydropyranyl; or tetrahydrothiopyranyl; $R^2$, $R^3$ and $R^4$ each are H or methyl; $R^5$ and $R^6$ each are H, methyl or methoxy; which comprises monoacylating, with a compound of the formula $R^1$—CO—Y wherein Y is halogen and $R^1$ has the values given above, a monoacid addition salt of a compound of the formula

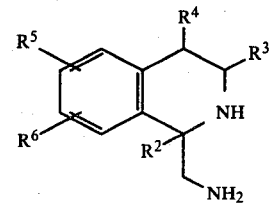

wherein $R^2$ through $R^6$ have the values given above wherein the monoacylation is carried out in the presence of a base which is more weakly basic than the monoacid salt and wherein the reaction temperature is 0°–100° C. and the reaction time is 24–0.5 hours.

2. The process of claim 1, wherein $R^1$ is cyclohexyl.

3. A process of claim 1 wherein the anion of the monoacid addition salt is chloride, sulfate, fluoride, bromide, iodide, phosphate, perchlorate or the anion of methane-, benzene-, or p-toluene-1- or 2-naphthalene-sulfonic acid.

4. A process of claim 3 wherein the anion is chloride or sulfate.

5. A process of claim 1 wherein the base is pyridine, quinoline, isoquinoline, 5-methyl-quinoline, acridine, dimethylaniline, p-anisidine, benzimidazole or phenanthridine.

6. A process of claim 1 wherein the reaction is carried out in the present of an inert solvent.

* * * * *